(12) United States Patent
Radmand

(10) Patent No.: US 11,033,750 B1
(45) Date of Patent: Jun. 15, 2021

(54) INTRA-ORAL APPLIANCE WITH THERMOELECTRIC POWER SOURCE

(71) Applicant: Achaemenid, LLC, Stratford, CT (US)

(72) Inventor: Reza Radmand, Boston, MA (US)

(73) Assignee: Achaemenid, LLC, Stratford, CT (US)

( * ) Notice: Subject to any disclaimer, the term of this patent is extended or adjusted under 35 U.S.C. 154(b) by 0 days.

(21) Appl. No.: 17/175,731

(22) Filed: Feb. 15, 2021

Related U.S. Application Data

(60) Provisional application No. 62/977,506, filed on Feb. 17, 2020.

(51) Int. Cl.

| | |
|---|---|
| *A61N 5/06* | (2006.01) |
| *A61N 1/36* | (2006.01) |
| *A61B 5/00* | (2006.01) |
| *C01B 33/20* | (2006.01) |
| *A61F 5/56* | (2006.01) |
| *H01L 35/00* | (2006.01) |
| *A61B 5/1455* | (2006.01) |
| *A61B 5/021* | (2006.01) |
| *A61B 5/0205* | (2006.01) |
| *A61B 5/08* | (2006.01) |

(Continued)

(52) U.S. Cl.
CPC ............ *A61N 5/0603* (2013.01); *A61B 5/682* (2013.01); *A61F 5/566* (2013.01); *A61N 1/3601* (2013.01); *C01B 33/20* (2013.01); *A61B 5/021* (2013.01); *A61B 5/0205* (2013.01); *A61B 5/026* (2013.01); *A61B 5/02405* (2013.01); *A61B 5/08* (2013.01); *A61B 5/14552* (2013.01); *A61B 5/291* (2021.01); *A61B 5/372* (2021.01); *A61N 2005/0606* (2013.01); *A61N 2005/0659* (2013.01); *H01L 35/00* (2013.01)

(58) Field of Classification Search
CPC ................ A61N 5/0603; A61N 1/3601; A61N 2005/0606; A61N 2005/0659; A61B 5/682; A61B 5/291; A61B 5/372; A61B 5/0205; A61B 5/021; A61B 5/02405; A61B 5/026; A61B 5/08; A61B 5/14552; A61F 5/566; C01B 33/20; H01L 35/00
See application file for complete search history.

(56) References Cited

U.S. PATENT DOCUMENTS

| | | |
|---|---|---|
| 3,599,629 A | 8/1971 | Gordy |
| 4,629,424 A | 12/1986 | Lauks et al. |

(Continued)

FOREIGN PATENT DOCUMENTS

| | | |
|---|---|---|
| AU | 2002100414 B4 | 11/2002 |
| CN | 1823691 A | 8/2006 |

(Continued)

OTHER PUBLICATIONS

US 10,350,107 B2, 07/2019, Kopelman (withdrawn)

(Continued)

*Primary Examiner* — Jonathan T Kuo
(74) *Attorney, Agent, or Firm* — Moyles IP, LLC

(57) ABSTRACT

An intraoral device includes a mouthpiece for receiving a dentition of a user. The intraoral appliance further includes an oxygen sensor and an infrared radiation emitter. The oxygen sensor may include a photoplethysmography sensor. The intraoral device may further include a thermoelectric power source to supply power to the infrared radiation emitter and the photoplethysmography sensor.

17 Claims, 3 Drawing Sheets

(51) Int. Cl.
*A61B 5/291* (2021.01)
*A61B 5/372* (2021.01)
*A61B 5/026* (2006.01)
*A61B 5/024* (2006.01)

(56) References Cited

U.S. PATENT DOCUMENTS

| | | | |
|---|---|---|---|
| 4,777,954 | A | 10/1988 | Keusch et al. |
| 5,190,053 | A | 3/1993 | Meer |
| 5,212,476 | A | 5/1993 | Maloney |
| 5,284,161 | A | 2/1994 | Karell |
| 5,490,520 | A | 2/1996 | Schaefer et al. |
| 5,765,563 | A | 6/1998 | Vander Schaaf |
| 5,792,067 | A | 8/1998 | Karell |
| 6,212,435 | B1 | 4/2001 | Lattner et al. |
| 6,418,933 | B1 | 7/2002 | Strong |
| 6,536,439 | B1 | 3/2003 | Palmisano |
| 6,598,006 | B1 | 7/2003 | Honda et al. |
| 6,604,527 | B1 | 8/2003 | Palmisano |
| 7,216,648 | B2 | 5/2007 | Nelson et al. |
| 7,690,378 | B1 | 4/2010 | Turcott |
| 7,711,438 | B2 | 5/2010 | Lattner et al. |
| 7,754,345 | B2* | 7/2010 | Tsai ............... C03C 8/16 428/689 |
| 7,885,708 | B2 | 2/2011 | Shanks et al. |
| 8,751,005 | B2 | 6/2014 | Meadows et al. |
| D718,448 | S | 11/2014 | Bedford et al. |
| D718,449 | S | 11/2014 | Bedford et al. |
| 10,195,426 | B2 | 2/2019 | Kent et al. |
| 10,195,427 | B2 | 2/2019 | Kent et al. |
| 10,206,570 | B2* | 2/2019 | McKenna ........... A61B 5/0002 |
| 10,251,774 | B2* | 4/2019 | Shah ................. A61B 5/682 |
| 10,376,202 | B2 | 8/2019 | Shah et al. |
| 10,376,210 | B2 | 8/2019 | Paris et al. |
| 10,420,672 | B2 | 9/2019 | Hermanson et al. |
| 10,470,921 | B2* | 11/2019 | Radmand ........... A61B 5/0816 |
| 10,862,508 | B1* | 12/2020 | Zhao ................. H03M 7/3044 |
| 2005/0113654 | A1 | 5/2005 | Weber et al. |
| 2007/0173893 | A1 | 7/2007 | Pitts |
| 2008/0220960 | A1* | 9/2008 | Tsai ............... C03C 8/16 501/19 |
| 2008/0233541 | A1 | 9/2008 | Vreese et al. |
| 2008/0300469 | A1 | 12/2008 | Kuo et al. |
| 2009/0082839 | A1 | 3/2009 | Lindquist et al. |
| 2009/0210032 | A1 | 8/2009 | Beiski et al. |
| 2009/0281433 | A1 | 11/2009 | Saadat et al. |
| 2010/0204614 | A1 | 8/2010 | Lindquist et al. |
| 2010/0204747 | A1 | 8/2010 | Lindquist et al. |
| 2010/0255447 | A1* | 10/2010 | Biris ................. C09D 189/00 433/201.1 |
| 2011/0213216 | A1* | 9/2011 | McKenna ........... A61B 5/0002 600/301 |
| 2013/0109932 | A1 | 5/2013 | Saadat et al. |
| 2013/0211270 | A1 | 8/2013 | St. Laurent et al. |
| 2013/0253286 | A1 | 9/2013 | Fridman |
| 2014/0114165 | A1* | 4/2014 | Walker ............... A61B 5/242 600/383 |
| 2014/0135868 | A1 | 5/2014 | Bashyam |
| 2014/0323839 | A1 | 10/2014 | McCreery |
| 2015/0190630 | A1 | 7/2015 | Kent et al. |
| 2015/0217115 | A1 | 8/2015 | Avitall |
| 2016/0199215 | A1 | 7/2016 | Kopelman |
| 2017/0196727 | A1 | 7/2017 | Giridharagopalan |
| 2017/0290699 | A1* | 10/2017 | Radmand ........... A61B 5/4557 |
| 2018/0000563 | A1 | 1/2018 | Shanjani et al. |
| 2018/0015282 | A1 | 1/2018 | Waner et al. |
| 2018/0116863 | A1* | 5/2018 | Shah ................. A61B 5/0878 |
| 2018/0177570 | A1 | 6/2018 | Alauddin et al. |
| 2019/0029587 | A1 | 1/2019 | Walker et al. |
| 2019/0057700 | A1 | 2/2019 | Kent et al. |
| 2019/0091061 | A1 | 3/2019 | Radmand |
| 2019/0133730 | A1* | 5/2019 | Adams .............. G06F 16/90335 |
| 2019/0343456 | A1 | 11/2019 | Kahlert et al. |
| 2020/0038231 | A1 | 2/2020 | Radmand |
| 2020/0060611 | A1 | 2/2020 | Radmand |
| 2020/0170574 | A1 | 6/2020 | Radmand |

FOREIGN PATENT DOCUMENTS

| | | | |
|---|---|---|---|
| CN | 104921833 | A | 9/2015 |
| EP | 3318216 | B1 | 2/2020 |
| JP | 2018000930 | A | 1/2018 |
| KR | 101645870 | B1 | 8/2016 |
| KR | 20160095425 | A | 8/2016 |
| WO | 2008048649 | A2 | 4/2008 |
| WO | 2012027648 | A2 | 3/2012 |
| WO | 2012027648 | A3 | 8/2012 |
| WO | 2014107446 | A1 | 7/2014 |
| WO | 2016087813 | A1 | 6/2016 |

OTHER PUBLICATIONS

Applied Thermoelectric Solutions, Introduction to Thermoelectrics and Medical Applications, Nov. 10, 2017, 33 pgs., https://thermoelectricsolutions.com/introduction-thermoelectrics-medical-applications/.

Arie Oliven, Treating Obstructive Sleep Apnea With Hypoglossal Nerve Stimulation, Medscape, Nov. 8, 2011, 9 pages, http://search.medscape.com/search/?q=Arie%20Oliven.

Bridgman et al., Mechanical Safety of Embedded Electronics for In-body Wearables: A Smart Mouthguard Study, dated Apr. 25, 2019, 36 pgs.

Castaneda, et al.; A review on wearable photoplethysmography sensors and their potential future application in health care; International Journal of Biosensors & Bioelectronics; dated Mar. 20, 2019; 19 pages.

European Respiratory Journal, Severity of obstructive sleep apnoea/hypopnoea syndrome and subsequent waking EEG spectral power, vol. 32, No. 3, Jun. 5, 2012, 6 pgs., https://erj.ersjournals.com/content/32/3/705. short.

International Searching Authority, International Search Report and Written Opinion of PCT App. No. PCT/US20/16597, dated Apr. 27, 2020, 16 pgs.

International Searching Authority, Written Opinion of PCT Publication No. WO2014107466, dated Mar. 19, 2014, 4 pages.

Kim et al., Biosens Bioelectron—Wearable salivary uric acid mouthguard biosensor with integrated wireless electronics, dated Aug. 1, 2015, 18 pgs.

Lissen Laboratories, Technology—Acostic Tooth Clip Sensor for Health, Jan. 23, 2020, 3 pgs., https://respiredx.com/index.php/technology/.

Lizette Borreli, Sleep Apnea May Increase Pneumonia Risk; CPAP May Increase Pulmonary Aspiration, Bacteria, Medical Daily, Mar. 3, 2014, 10 pages, http://www.medicaldaily.com/.

Nabavi et al, A Smart Mandibular Advancement Device for Intraoral Cardiorespiratory Monitoring, Conference in Montreal Canada—Jul. 20-24, 2020, 6 pgs. https://ieeexplore.ieee.org/document/9176520.

National Institute of Health Public Access Author Manuscript, EEG Recording and Analysis for Sleep Research, Oct. 2009, 21 pgs., https://www.ncbi.nlm.nih.gov/pmc/articles/PMC2824445/.

Norman Wolkove, et al., Long-term compliance with continuous positive airway pressure in patients with obstructive sleep apnea, Oct. 2008, 8 pages, www.ncbi.nlm.nih.gov/.

Nyxoah, Enjoy the comfort of Restful Nights, What is OSA?, Aug. 27, 2016, 3 pages, http://www.nyxoah.com/patients/what-is-osa.

Nyxoah, Sleep Apnea, Nyxoah, 2015, 5 pages, http://www.nyxoah.com/sleep-apnea.

Researchgate, Sublingual electrical stimulation of the tongue during wakefulness and sleep, Sep. 2001, 1 page, https://www.researchgate.net/publication/11839659.

Seshadri et al; Wearable Sensors for COVID-19: A Call to Action to Harness Our Digital Infrastructure for Remote Patient Monitoring and Virtual Assessments; Frontiers in Digital Health, vol. 2; Jun. 23, 2020; 11 pages.

(56) References Cited

OTHER PUBLICATIONS

Silva et al., Development and Implementation of an Intraoral Device for Occlusal Stability during Sports Performance: A Case Report, dated Nov. 8, 2018, 28 pgs.

Sporttechie, Pilot Program Has Select NFL Teams Wearing Sensor-Laden Mouth Guards to Study Concussions, Aug. 28, 2019, 3 pgs., https://www.sporttechie.com/nfl-mouth-guard-sensors-concussion-technology.

Tec Microsystems, Miniature Thermoelectric Generators, Aug. 14, 2020, 5 pgs., https://www.tec-microsystems.com/products/thermoelectric-generators/index.html.

Tekscan, Inc., Measure Force with FlexiForce Force Sensors, 8 pages, Apr. 12, 2015, https://www.tekscan.com/product-group/embedded-sensing/force-sensors.

True Wearables, Oxxiom—Expand Your Limits Control What You Can Measure Aim Higher, 2015, 5 pgsl., https://www.truewearables.com/.

United States Patent and Trademark Office, Office Action of U.S. Appl. No. 16/152,778, dated Sep. 14, 2020, 9 pgs.

United States Patent and Trademark Office, Office Action of U.S. Appl. No. 16/781,417, dated Apr. 16, 2020, 14 pgs.

United States Patent and Trademark Office; Advisory Action Before the Filing of an Appeal Brief for U.S. Appl. No. 16/781,417; dated Feb. 3, 2021; 3 pages.

United States Patent and Trademark Office; Final Office Action for U.S. Appl. No. 16/781,417; dated Nov. 17, 2020; 17 pages.

Vatansever et al., Far infrared radiation (FIR): Its biological effects and medical applications, Photon Lasers Med 2012; 12 pgs.

Very Well Health, Electronic Tongue Device for Sleep Apnea, dated Apr. 29, 2019, 4 pgs., https://www.verywellhealth.com/hypoglossal-nerve-stimulator-for-treating-sleep-apnea-3015195.

Wikipedia, Pulse Oximetry, Wikipedia, Oct. 1, 2004, 9 pages, https://en.wikipedia.org/wiki/Pulse_oximetry.

United States Patent and Trademark Office; Notice of Allowance for U.S. Appl. No. 16/202,204; dated Mar. 15, 2021; 10 pages.

* cited by examiner

INTRA-ORAL APPLIANCE WITH THERMOELECTRIC POWER SOURCE

CROSS-REFERENCE TO RELATED APPLICATIONS

This application claims the benefit of U.S. Provisional Application No. 62/977,506 filed Feb. 17, 2020, which is incorporated herein by reference in its entirety.

BACKGROUND

Sleep apnea is a common medical condition during which a person experiences one or more pauses in breathing, and, in some instances, experiences shallow breaths during sleep. While there are several types of sleep apnea, the most common type is obstructive sleep apnea. In this medical condition, one or more of the person's throat muscles relax during sleep causing surrounding tissues in the posterior portions of the mouth, nose, and throat to collapse, thereby creating a pharyngeal obstruction that can block the upper airway. Persons suffering from obstructive sleep apnea have inadequate oxygen exchange during sleep, which can lead to daytime fatigue, lack of concentration, and mood changes. Left untreated, obstructive sleep apnea can have a significant impact on a person's health, often leading to cardiovascular, stroke, and metabolic disorders.

Known methods for treatment of obstructive sleep apnea include both surgical and nonsurgical devices. A popular surgical procedure is uvulopalatopharyngoplasty, which may be performed for patients who have anatomical abnormalities that cause their obstructive sleep apnea and/or make them less likely to tolerate nonsurgical devices. Uvulopalatopharyngoplasty may be a complicated surgery, during which a portion of the soft palate is removed in an effort to prevent closure of the airway by excess tissue during sleep. A disadvantage of this procedure, however, is that the operation is often expensive, may damage throat muscles necessary for swallowing, and/or cause other undesirable disorders, such as nasal regurgitation and numbness of the lower front teeth.

To reduce this risk, various nonsurgical approaches have been employed. One such nonsurgical approach includes using standardized oral appliances to incrementally advance and/or protrude the mandible (lower jaw) relative to the maxilla (upper jaw). These standardized oral appliances, commonly referred to as a mandibular advancement device, ("MAD"), typically include upper and lower dental trays. The lower dental tray is designed to advance the mandible and move the tongue forward to increase the space in the posterior part of the throat and the oropharynx, which in turn may serve to increase the flow of air during sleep. The distance (degree of advancement) required to protrude and/or reposition the mandible may be dependent, at least in part, on the severity of the individual's obstructive sleep apnea, as well as physiological variables among the users. A disadvantage of using these standard oral appliances is that they may not address individualized anatomical variances such as difference in dental arches, dentition alignment, and/or jaw flexibility. Another disadvantage is that in instances where the degree of advancement is excessive, the appliance may lead to long-term temporomandibular joint ("TMJ") disorders, muscular aggravation, dentition discomfort, and/or myofascial disorders. As a result, use of these standard appliances has an approximate compliance rate of 75% over a 2-year period. Thus, such oral appliances may not treat obstructive sleep apnea in a manner that prevents and/or limits adverse impacts on a person's health.

Other methods of treating obstructive sleep apnea include the administration of positive air pressure via a continuous positive airway pressure ("CPAP") machine. The CPAP machine is often assembled for use in combination with various face or nasal masks and may provide continuously pressurized and/or forced air during the person's sleep. A disadvantage of this assembly is that it may cause nasal and/or oral mucosal dryness due to the continuously forced air and may also cause claustrophobia due to the presence of a mask on the patient's face. As a result, use of these assemblies has an approximate compliance rate of 50% over a 5-year period. Another disadvantage is that standard masks are not properly adapted for a customized fit for persons with unique and/or variable facial anatomies that may be natural or created by loss of muscle tone secondary to facial paralysis and/or stroke. Ill-fitting masks may lead to leakage of air and/or inadequate air intake. In addition, the masks used with CPAP machines have been found to be a breeding ground for bacteria and fungi. Despite routine washing and cleaning measures, the bacteria and fungi on these masks can grow exponentially, and lead to infections, such as pneumonia, in the airways of persons who use them. Moreover, such assemblies may not sufficiently treat obstructive sleep apnea and may fail to promote patient compliance with the treatment method.

The aforementioned treatment techniques may not provide sufficient treatment of obstructive sleep apnea, may cause other negative health situations for the user, and may not foster compliance with treatment methods.

Non-invasive physiological sensors are applied to the body for monitoring or making measurements indicative of a patient's health. One application for a non-invasive physiological sensor is pulse oximetry, which provides a noninvasive procedure for measuring the oxygen status of circulating blood. Oximetry has gained rapid acceptance in a wide variety of medical applications, including surgical wards, intensive care units, neonatal units, general wards, home care, and physical training. A pulse oximetry system generally includes a patient monitor, a communications medium such as a cable, and a physiological sensor having light emitters and a detector, such as one or more LEDs and a photodetector. The sensor is attached to the outer surface of a body component of a user, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation ($SpO_2$) and pulse rate. Such externally oriented pulse oximeters may be the subject of numerous motion artifacts, ambient light exposure to the sensor diode and fail to accurately capture data related to the $SpO_2$ and pulse rate of the user.

Conventional monitoring of sleep apnea disorders relies on the use of separate medical devices dedicated to monitor each of the variables listed above. For example, pulse oximeter sensors are used to measure $SpO_2$ and pulse rate typically from a finger probe attached to the patient by a cable. Similarly, respiratory rate is typically measured by a nasal cannula or chest belt which require a bulky set-up. Likewise, EEG recording typically requires the placement of biopotential electrodes on the scalp which can fall off during prolonged data recording applications. Being tethered to multiple monitoring equipment can interfere with comfortable and natural sleeping which poses a major impediment during sleep studies that are conducted by clinicians to diagnose sleep disorders and the effectiveness of prescribed treatments. In addition, preparing the recording set-up is expensive and time consuming and rely on skilled medical personal. Recording physiological data from multiple monitors can contribute to diagnostic uncertainty due to the inherent instrumental time delays between physiological changes that occur naturally inside the body and the data recorded separately by each monitor.

There is a need for a device and method capable of overcoming the above limitations. There is a further need for a device and method capable of determining when a user is having arousals or being awoken from deep sleep, entering or in an obstructive sleep apnea condition. There is yet a further need for a device and method of capturing a user's bio-signal measurements. There is a further need for a device having a self-sustaining energy source for capturing a user's bio-signal measurements.

BRIEF SUMMARY

Embodiments of the disclosure are associated with an intraoral device. The intraoral device includes a mouthpiece for receiving a dentition of a user. According to an aspect, the mouthpiece includes a red light and various wave lengths of an infrared radiation emitter and an oxygen sensor for measuring an oxygen saturation level of the user's blood.

Embodiments of the disclosure may be associated with an intraoral device including a mouthpiece for receiving a dentition of a user, and a photoplethysmography sensor secured to the mouthpiece. According to an aspect, the photoplethysmography sensor monitors at least one of a cardiac condition, a respiratory condition, perfusion index, heart rate variability, irregular heartbeat, such as atrial fibrillation, and a blood pressure condition of the user. These parameters may be predictors of cardiovascular risk factors.

Additional embodiments of the disclosure may be associated with an oral appliance including a mouthpiece, red light and infrared radiation emitter secured to the mouthpiece, a photoplethysmography sensor secured to the mouthpiece, and a rechargeable battery or a thermoelectric power source configured to supply power to the photoplethysmography sensor. The mouthpiece is configured for being positioned in an oral cavity of a user. According to an aspect, the red light and infrared radiation emitter dilates the blood vessels of the user and the photoplethysmography sensor captures bio-signal measurements of the user, via the dilated blood vessels.

BRIEF DESCRIPTION OF THE DRAWINGS

A more particular description will be rendered by reference to exemplary embodiments that are illustrated in the accompanying figures. Understanding that these drawings depict exemplary embodiments and do not limit the scope of this disclosure, the exemplary embodiments will be described and explained with additional specificity and detail through the use of the accompanying drawings in which.

Figure 1:
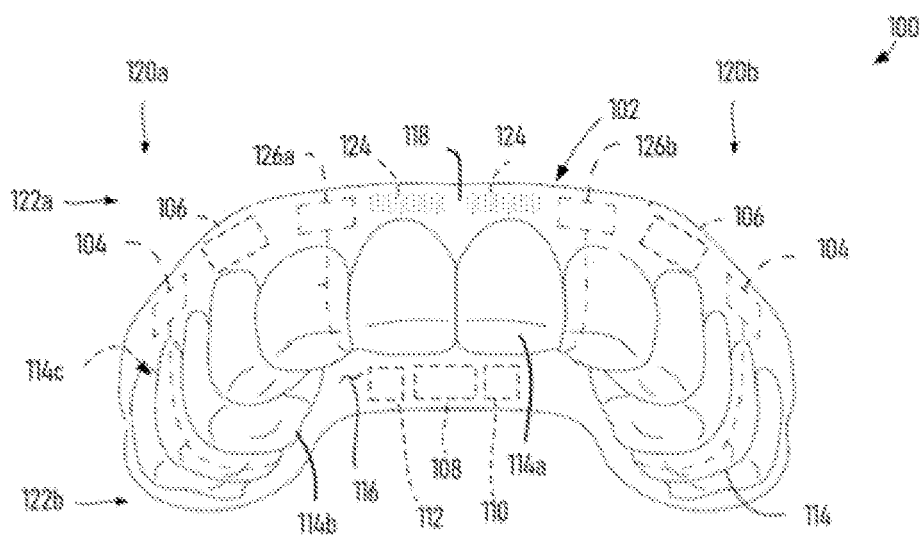
FIG. 1 illustrates an intraoral device, according to an embodiment.

Various features, aspects, and advantages of the exemplary embodiments will become more apparent from the following detailed description, along with the accompanying drawings in which like numerals represent like components throughout the figures and detailed description. The various described features are not necessarily drawn to scale in the drawings but are drawn to aid in understanding the features of the exemplary embodiments.

The headings used herein are for organizational purposes only and are not meant to limit the scope of the disclosure or the claims. To facilitate understanding, reference numerals have been used, where possible, to designate like elements common to the figures.

DETAILED DESCRIPTION

This disclosure generally relates to an intraoral device or an intraoral oxygen monitor. More particularly, this disclosure is directed to an intraoral device for measuring the oxygen saturation level in the blood of a user, also referred to as SpO2, which is a measure of the amount of oxygen-carrying hemoglobin in the blood relative to the amount of hemoglobin that is not carrying oxygen.

The intraoral oxygen monitor may generally include a mouthpiece for receiving the user's dentition, at least one of a red light, near infrared (IR) and far infrared radiation (FIR) emitter for dilating the user's blood vessels (i.e., causing vasodilation and at least one oxygen sensor for measuring the oxygen saturation level (SpO2) of the user's blood. The intraoral oxygen monitor may also include an energy source for providing power to the red light, near IR and FIR emitter(s), oxygen sensor(s), and/or any other components present in the mouthpiece. The energy source may be self-sustaining, for example, a thermoelectric device. According to an aspect, the energy source is a rechargeable battery.

The intraoral oxygen monitor may find use in the diagnosis and/or treatment of various conditions, including, but not limited to, sleep disorders, head trauma, or the like, or in various other activities, such as athletics, hobbies, or other recreational activities.

FIG. 1 schematically depicts an exemplary intraoral device 100, more particularly, an intraoral oxygen monitor. Generally described, in the illustrated example, the intraoral device 100 includes a mouthpiece 102, at least one infrared emitter (such as, a red light, near infrared (IR) and far infrared radiation (FIR) emitter) 104 for dilating the user's blood vessels, and at least one oxygen sensor 106 for measuring an oxygen saturation level in the user's blood. The intraoral device 100 may also include a battery or other energy source 108 for providing power to the at least one red light, near IR or the FIR emitter(s), the oxygen sensor(s), and/or any other components present in the mouthpiece. Such other components may include, but are not limited to, a microprocessor 110, a data recorder 112, and/or various other elements described below. The battery may be a rechargeable battery. According to an aspect, the battery is a lithium ion battery.

Viewing each component of the intraoral device 100 in greater detail, the illustrated mouthpiece 102 is configured to be worn on an upper dentition of a user. As illustrated in FIG.

1, the mouthpiece 102 includes a dentition receiving portion 114, which has a generally arch shape of an upper dentition. The dentition receiving portion 114 has a buccal surface/ wall/portion 114a facing the user's lips and/or cheeks, a lingual surface/wall/portion 114b opposite the buccal surface facing the user's tongue, and a central channel 114c bounded by the buccal wall 114a and the lingual wall 114b. When the mouthpiece 102 is in use, the central channel 114c receives the user's dentition and extends over and/or covers occlusal or bite surfaces of the user's teeth, the lingual wall 114b of the mouthpiece extends between the user's teeth and the user's tongue, and the buccal wall 114a of the mouthpiece extends between the user's teeth and the user's cheek.

The mouthpiece 102 further includes a palate covering portion 116 adjacent to and integrally connected with the lingual wall 114b of the dentition receiving portion 114. The palate covering portion 116 extends along at least a portion of the user's hard palate. The mouthpiece 102 also includes a gum covering portion 118 integral with and extending upwardly from the buccal wall 114a of the dentition receiving portion 114, such that the gum covering portion 118 lies along the user's upper gum adjacent to the user's maxillary bone. The dentition receiving portion 114, palate covering portion 116, and gum covering portion 118 may be integral parts of a unitary body.

The gum covering portion 118, dentition receiving portion 114, and mouthpiece 102 overall can each be described (e.g., when viewed in top plan view) as having a left side/portion/ wing 120a (i.e., generally positioned on the user's left dentition), a right side/portion/wing 120b (i.e., generally positioned on the user's right dentition), an anterior portion or end 122a (i.e., generally positioned on the user's front/ anterior dentition), and a posterior portion or end 122b (i.e., generally positioned on the user's back/posterior dentition). The palate covering portion 116 thus extends between and is partially surrounded by the left side 120a of the dentition receiving portion 114 and the right side 120b of the dentition receiving portion 114.

The emitter 104, such as a FIR emitter, may be any suitable component or device capable of emitting infrared radiation. The emitted IR improves microvascular vasodilation, which makes the vascular flow more readily available (e.g., closer to the tissue surface), which may in turn, improve the accuracy of the SpO2 measurement (discussed below). According to an aspect, the emitter 104 is a FIR emitted that emits infrared radiation (i.e., at a wavelength range of from about 3 to about 100 micrometers). IR, such as FIRm may also be absorbed by water molecules, which may result in the generation of heat that can be emitted from the oral mucosa (i.e., tissue), which may also improve blood flow and improve the accuracy of the SpO2 measurement.

The oxygen sensor 106 monitors and determines the oxygen saturation levels (SpO2) of the user's hemoglobin. The oxygen sensor(s) also monitor and determine the pulse and/or heart rate of the user. In some embodiments, at least one oxygen sensor 106 may be a transceiver such as a pulse oximeter that monitors or detects the oxygen saturation level by analyzing the change in color of the user's blood. More particularly, the pulse oximeter may include light emitting diodes that transmit red and infrared lights to vascular surfaces of the user's tongue and sense changes in oxygen level. The pulse oximeter may also calculate the pulse rate and/or heart rate of the user, typically in beats per minute, based on variations and/or deviations in the user's oxygen saturation level.

Figure 2:
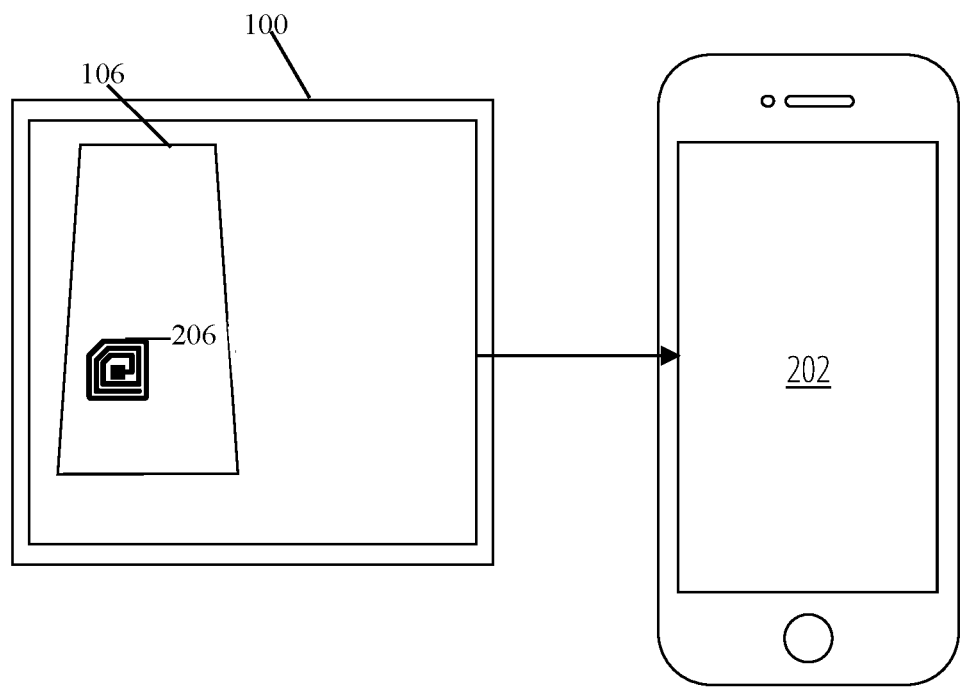
FIG. 2 illustrates an intraoral device including an oxygen sensor, according to an embodiment.
Figure 3:
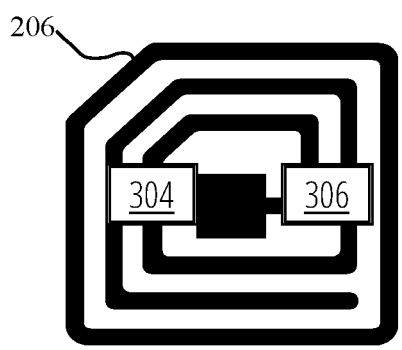
FIG. 3 illustrates a photoplethysmography sensor configured for use with an intraoral device, according to an embodiment.

In some embodiments and as illustrated in FIG. 2, an oxygen sensor 106/pulse oximeter includes an integrated photoplethysmography (PPG) (i.e., an optically obtained plethysmogram) sensor 206. As illustrated in FIG. 3, the PPG sensor 206 includes a light source 304 and a photodetector 306 positioned to take measurements of volumetric variations in the blood circulated in the user's oral cavity. The light source 304 is configured to emit light to the user's oral mucosa and the photodetector 306 is configured to measure the light reflected from the user's gum or oral mucosa. The PPG sensor 206 generates data or a waveform that can be interpreted and provide pertinent health-related information. The photodetector 306 may include an integrated microcontroller (not shown) for analyzing raw data received by the photodetector. According to an aspect, the photodetector 306 includes a communication structure for outputting the raw data to an external computing device, such as a computer of a mobile phone 202.

According to an aspect, the integrated PPG sensor 206 monitors various other physiological states, conditions, or events. Such states, conditions, or events may relate to cardiac/circulatory issues (e.g., changes in circulation, low blood perfusion, irregular heart beat (i.e., arrhythmia), pulse rate, cardiac output (i.e., changes in blood volume, especially in disease conditions), heart rate variability (HRV) (also referred to as cycle length variability, RR variability, or heart period variability), respiration/respiratory issues (e.g., changes in respiration), and/or blood pressure (e.g., changes in blood pressure).

According to an aspect, the physiological states monitored or otherwise captured by the integrated PPG sensor 206 may help provide data that is indicative of the user suffering from community-based illnesses/community diseases, respiratory diseases such as communicable or infectious diseases spread through the air, surfaces, people, foods and animals. Such communicable diseases include, but are not limited to influenza, COVID-19, and the like. The intraoral device 10 may capture increases in temperature, heartrate and respiratory rate, which may precede the onset of such communicable diseases. For example, the integrated PPG sensor 206 may indicate that the user has a low oxygen level, which may be an early indication that the user may need medical care. According to an aspect, the integrated PPG sensor 206 may communicate with the external computing device when the user's oxygen levels is below 90%. The PPG sensor 206 may communicate with the external computing device when the user's oxygen levels is below 88%.

While typical PPG signals captured by, for example, smart watches and other wearable devices are susceptible to motion artifacts caused by hand movements and ambient light dilution, the integrated PPG sensor 206 of the intraoral device 100 device eliminates such ambient light and motion artifacts. Using the PPG sensor 206, the intraoral device 100 may monitor the user's heart rate during the user's daily routine activities and during strenuous activities or physical exercise. The PPG sensor 206 may also be configured to filter out environmental noise, which may negatively affect the quality of the PPG signal sought to be acquired and consequently affect the estimation accuracy of the user's heart rate. According to an aspect, the PPG sensor 206 captures signals indicative of SpO2 levels with an error rate of 3% or below. The error rate may be about 1% or below. The integrated PPG sensor 206 may be stabilized by the user's dentition and, generally, the user's oral anatomical structures (dentition, gum overlying the jaw, and the like). By virtue of being located in the oral cavity, the integrated PPG sensor 206 is isolated from outside ambient light exposure and outside temperature variations, which may alter or affect vascular flow and skew the PPG signals.

According to an aspect, the integrated PPG sensor 206 is configured to determine the respiratory rate of the user. The integrated PPG sensor 206 may capture data related to the frequency, intensity, and amplitude (i.e., depth of breathing) of the user's respiratory rate. The frequency and amplitude of the heart-related variations are typically modulated by respiration, with the heart rate typically increasing during inspiration and decreasing during expiration, which may change the statistical characteristics of the PPG signal.

The PPG signal captured by the integrated PPG sensor 206 may be able to record the electrical signals from the user's heart. According to an aspect, the integrated PPG sensor 206 captures electrocardiogram (ECG) data for assessing Heart Rate Variability (HRV) signals, which aid medical professionals, researchers, and clinicians in their evaluation of cardiovascular related illness and diseases. The HRV signals captured by the integrated PPG sensor 206 may provide data that helps a medical professional diagnose atherosclerosis and arterial stiffness by capturing the pulsed tone or arterial tone of the user. It is contemplated that data captured pertaining to the pulsed tone may also be utilized to predict future cardiovascular problems. Once the PPG sensor 206 captures data related to arterial stiffness, an estimation of how much blood the left ventricle pumps out (i.e., left ventricular ejection fraction) may be calculated and heart failure can be determined.

The integrated PPG sensor 206, via its generated PPG signal, may detect information that facilitates identification and diagnosis of various cardiovascular diseases, such as, cardiomyopathy and arrythmia. The PPG signal may provide information indicative of blood volume changes in a user. Such blood volume changes may be calculated based on the amount of light detected by the integrated PPG sensor's 206 photodetector 306. In addition, PPG sensors are also useful in the determination of hyperemia, or an excess of blood flow.

The integrated PPG sensor 206 may generate an acceleration photoplethysmogram (APG), which may be determined from the PPG signal. Analysis of the APG of the PPG signal may aid in the early detection and diagnosis of various cardiovascular diseases that typically occur later in a user's life. According to an aspect, the APG may be used to detect and to diagnose cardiac abnormalities of the user. The APG generated by the integrated PPG sensor may directly correlate to the user's blood pressure, vascular age, risk of coronary art disease, the distensibility of the user's carotid artery and indicate the presence of atherosclerotic disorders.

According to an aspect, the PPG sensor 206 acquires multiple physiological variables simultaneously in real-time, it is cost-effective, it is convenient to wear, easy to activate with the use of a thermal sensor (positioned in the mouthpiece) as soon as the intraoral device 100 is placed in the user's oral cavity. Once the PPG sensor detects and arrives at the user's core (i.e., body) temperature, the PPG sensor is activated and begins to capture the physiological data. Upon removal of the intraoral device 100 from the user's oral cavity, the thermal detector notes the temperature change outside of the oral cavity and stops detecting data. This function also allows the PPG sensor to act as a compliance recorder for that specific user, hence allowing the PPG sensor to act as a time stamp for actual utilization of the intraoral device 100. This is especially critical in federal and state licensing requirements for pilots, heavy trucks and machinery operators. This feature may be particularly suited for the use of customized mouthpiece where the duration of the use of the intraoral appliance 100 is important in obtaining therapeutic levels of sleep.

It is contemplated that the integrated PPG sensor measures physiological changes from the oral cavity during hypoxemia much faster because the sensor is located closer to the heart and lungs where these physiological changes originate in the body, as compared to, for example, measurement obtained by a finger pulse oximeter from a peripheral site. This time difference can be significant in trying to detect abrupt changes associated with sleep apnea.

The emitter(s) 104 and the oxygen sensor(s) 106 may be positioned near (e.g., joined to or at least partially embedded within) the anterior end/portion 122a of the mouthpiece, i.e., towards the user's lips and away from the user's pharynx or posteriorly, proximal to the cheek side. For example, the emitter(s) 104 and the oxygen sensor(s) 106 may be provided along the gum covering portion 118 along the buccal regions of the upper jaw (as shown), or along the lingual wall 114b of the mouthpiece 102 adjacent to the lateral portions of the tongue (which are generally understood to be the most vascular areas of the tongue). It will be appreciated that, while the oxygen sensor(s) 106 and the emitter(s) 104 are illustrated as separate components in the exemplary embodiment, it is also contemplated that the oxygen sensor(s) 106 and the emitter(s) 104 may be part of the same component or device. It will also be appreciated that, while the oxygen sensor(s) 106 and the emitter(s) 104 are shown as being integrated into a mouthpiece for the user's upper dentition, the oxygen sensor(s) 106 and the emitter(s) 104 may alternatively be integrated into a mouthpiece for lower dentition, as will be discussed below. Furthermore, while FIG. 1 illustrates two emitters 104 and oxygen sensors 106, other numbers of emitters and oxygen sensors may be used.

If desired, the mouthpiece 102 may be impregnated with ceramic nanoparticles 124, for example, boron silicate particles. Such particles are known to emit FIR when exposed to heat. Heat from the oral cavity may thus be used to generate FIR, which can then be transferred either through direct contact with the oral tissue via conductance or conveyance via air to cause the tissue vasodilation. Since the user's core temperature will generally be maintained, this transfer of FIR may be considered self-sustaining and repeatable. It is also believed that such particles may be used to generate medium IR or even possibly red light, which is needed for measuring SpO2. While not wishing to be bound by theory, it is also believed, that this may eliminate the need for use of a battery. At the very least, the ceramic nanoparticles 124 may reduce the energy needed for a battery to operate the sensors.

Figure 4:
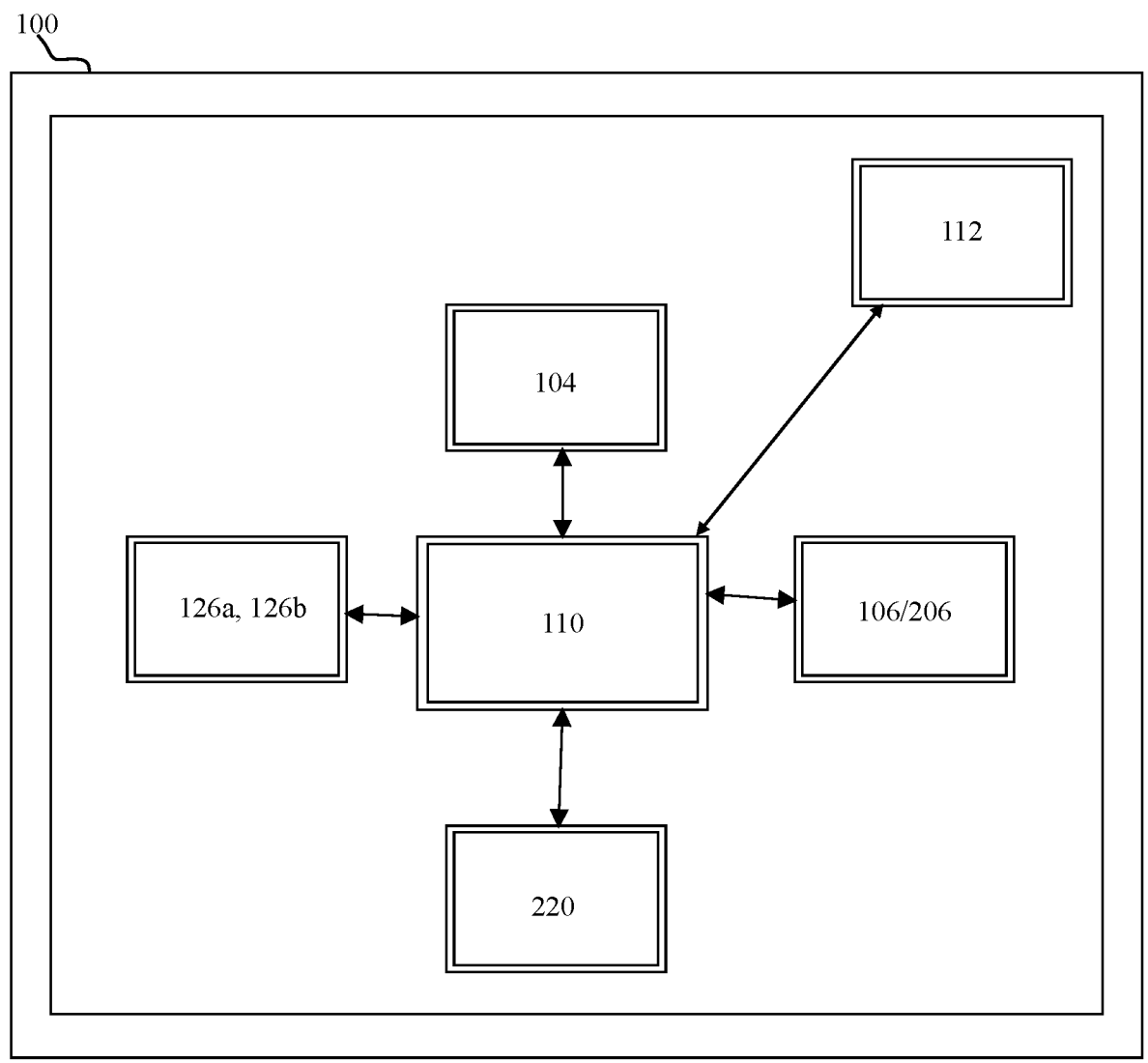
FIG. 4 is a chart illustrating a microprocessor in communication with components of an intraoral device, according to an embodiment.

FIG. 4 illustrates the intraoral device 100 including other components, such as a microprocessor 110 for analyzing/processing data and a data recorder/transmitter 112 for sending data to local or remote storage (not shown), as will be understood by those of skill in the art. In the illustrated example, the microprocessor 110 and data recorder/transmitter 112 are shown as being provided along the palate covering portion 116 of the mouthpiece 102. However, other locations may be suitable.

As illustrated in FIG. 1, the power source 108 may be a battery (e.g., replaceable or rechargeable). Alternatively, the power source 108 may be a self-sustaining power source, such as a thermoelectric device. For example, the power source 108 may be a patch of thermoelectric material having an area of at least about 1 sq. cm and a thickness of at least about 0.5 mm, at least partially embedded within the mouthpiece 102. Any suitable thermoelectric material may be used to form such a power source, such as those provided by TEC Microsystems, Inc. Such materials can be joined to or integrated into the intraoral device to capture body heat and convert it into electricity that can be used by the oxygen sensor, emitter, and/or other components within the appliance, thereby reducing or eliminating the need for batteries or external charging and forming a closed (or at least partially closed) energy system. In the illustrated example, the power source 108 is shown as being provided along the palate covering portion 116 of the mouthpiece 102. However, other locations may be suitable.

The intraoral device 100 may have numerous variations, and/or may be used in combination with other components and/or devices. For example, the device may include a pressure sensor, an airflow sensor, a noise detector, an actigraphy sensor, or any combination thereof, which may be useful in detecting or studying various conditions, for example, sleep apnea or other sleep disorders.

According to an aspect, the intraoral device 100 may be used in combination with electrodes 126a, 126b to measure activity within the user's brain. More particularly, electrodes 126a, 126b positioned along the gum covering portion 118 of the mouthpiece 102 adjacent the buccal side of the maxillary bone of the user (i.e., between the upper gums and inner lip/cheek of the user) may be used in combination with the microprocessor 110 as an electroencephalograph (EEG) for detecting electrical activity in the user's brain. In such an embodiment, the EEG electrodes 126a, 126b may be part of an upper mouthpiece (e.g., mouthpiece 102) with the oxygen sensor 106 and/or the emitter 104, or the EEG may be part of an upper mouthpiece (e.g., mouthpiece 104) and either one of (or both of) the oxygen sensor 106 and/or the emitter 104 could be part of a lower mouthpiece (not shown) separate from or connected to the upper mouthpiece.

Such a device may be useful as a mouthguard for use in a variety of applications. In one example, the device 100 may be useful in diagnosing and/or treating sleep disorders, such as sleep apnea, and/or for generally monitoring or determining the sleep state activity of the user. The device 100 may be configured to track the stages of a user's sleep, in both REM and non-REM stage. As another example, the device 100 may find use as a "smart" mouthguard for athletic activities. The mouthguard may be used to assess potential medical conditions or injuries, such as concussions or other head trauma. The data measured by the PPG sensor may be transmitted utilizing low-energy wireless Bluetooth technology to a compatible wireless receiver in a smart device or can be delivered to a remote application via the internet (e.g., a cloud application). Dedicated software algorithms executed in the receiver log the data, compute and display arterial oxygen saturation, pulse rate, pulse rate variability, blood perfusion index, respiratory rate, and EEG information to assess sleep stages, diagnose OSA and for follow-up monitoring of patient treatment. The PPG sensor and rechargeable battery are encapsulated in a custom-fit molded mouthpiece worn in the mouth. The intraoral device 100 may be used conveniently in clinical settings and home recording over extended periods of time with little subject interference.

Other possibilities are contemplated, as will be understood by those of skill in the art. Such data may also be useful in generally studying head trauma that occurs in athletics. As another example, the various mouthpieces may find use in hobbyist or gaming applications, such as personal meditation devices, virtual reality games, video games, learning/educational devices, or other personal activities that center around brain activity. The mouthpiece 104, which embodies the PPG sensor and/or EEG electrodes, can be used by the military to monitor the health and stamina of the soldiers on and off the field. Each mouthpiece 104 may be customized and tagged to the specific person wearing the intraoral device 100. The data obtained from each intraoral device 100 can be tracked and recorded accordingly.

According to another aspect, the SpO2 data, alone or in combination with EEG data (and any other data collected via other sensors/components) may be used in connection with a stimulator 220 (FIG. 4) to stimulate the genioglossus muscle of the user's tongue. For example, the stimulator 220 may be activated if the oxygen sensor determines that the actual oxygen saturation level of hemoglobin of the user is beneath a predetermined level. Alternatively or additionally, if the EEG data indicates that the user has been aroused from sleep unexpectedly, the microprocessor 110 may cause the stimulator 220 to send impulses to stimulate the genioglossus muscle of the user's tongue.

The stimulation may be in the form of electrical impulses that cause the genioglossus muscle to contract and/or cause the user to reduce the amount of force being applied to occlusal and/or bite surfaces of the user's teeth. The stimulation may also cause contraction of the genioglossus muscle, which may cause the user's tongue to protrude, thereby creating more space in the user's pharynx to help the user breathe more easily in a manner that increases the oxygen saturation levels of the user's hemoglobin.

In this example, the stimulator 220 may be provided on a mouthpiece configured for receiving lower dentition of the user. The stimulator 220 may be provided near the posterior portion of the lower mouthpiece, that is generally near the back of the user's mouth, for example, on the lingual portion of the mouthpiece adjacent to the tongue. The stimulator 220 may be positioned substantially adjacent to a base of the user's tongue, for example, adjacent to the user's genioglossus muscle. The stimulator 220 may be bilaterally positioned on the mouthpiece, such that bilateral stimulation may be provided to both sides of the user's tongue. The other components (including the oxygen sensor(s) and the emitter(s) may be part of the lower mouthpiece, or may be part of an upper mouthpiece, as described above. One example of an oral device including a stimulator 220 for stimulating the genioglossus muscle of a user is described in U.S. Pat. No. 10,470,921B2, issued Nov. 12, 2019, which is incorporated by reference herein in its entirety.

Additionally or alternatively still, the present intraoral device 100 may be used in combination with a mandibular advancement device (MAD) (not shown), as are known to be used in the treatment of sleep apnea. MAD devices are generally operative for advancing a lower jaw of the user relative to a upper jaw of the user. In such an instance, the various data collected by the intraoral device 100 (e.g., the SpO2 data) may be used to assess whether the MAD has been adjusted appropriately (i.e., such that the protrusive distance of the lower jaw is sufficient), or whether additional adjustment is needed to improve treatment. One example of a MAD that may be suitable for use with the present disclosure is described in PCT Publication WO 2019/094744A1, published May 16, 2019, which is incorporated by reference herein in its entirety. However, countless other MAD devices may be used in connection with the present disclosure.

EXAMPLES

Oral appliances were built to assess whether a self-contained oral appliance could accurately capture bio-signal measurements. The oral appliances were set up to conduct measurements of SpO2 in the oral cavity of a user and report data corresponding to the measured SpO2, recorded or in real-time. The oral appliance was constructed to fit the mandible (i.e., the lower jaw).

Three oral appliances were constructed—Sample 1, Sample 2, and Sample 3. Each oral appliance included a mouthpiece and two PPG sensors attached to the mouthpiece. The PPG sensors were positioned at two different areas of the mouthpiece so that they would contact the lower gum portion of a user's mouth. A first PPG sensor was positioned to contact the front gum line and a second PPG sensor was positioned to contact the left-side molar gum line. The PPG sensors were each connected to a pulse oximeter (i.e., a Masimo Radical SET pulse oximeter).

TABLE 1

|  | SpO2 Error Rate (%) | | | Pulse Rate Error Rate (%) | | |
| --- | --- | --- | --- | --- | --- | --- |
|  | Test 1 - Motionless | Test 2 - Post-Exercise | Test 3 - Bag Breathing | Test 1 - Motionless | Test 2 - After Exercise | Test 3 - Bag Breathing |
| Sample 1 | 0.3 | 0.4 | 1 | 1 | 2.3 | 0.6 |
| Sample 2 | 0.2 | 0.3 | 0.1 | 1.8 | 0.6 | 0.5 |
| Sample 3 | 0.6 | 0.4 | 1.3 | 1.1 | 0.5 | 0.6 |
| Average | 0.4 | 0.4 | 0.8 | 1.3 | 1.1 | 0.6 |

Three different tests were devised to evaluate the effectiveness of Sample 1, Sample 2, and Sample 3. The first test recorded the SpO2 and pulse rate (PR) of the user while the user remained motionless/sat still, thereby serving as a control and providing an environment that limited potential source-related errors. The second test recorded the SpO2 and PR of the user after the user exercised by running up a flight of stairs, indicating that the user's PR increased and the user's $SpO_2$ levels remained in a normal range. The third test recorded the $SpO_2$ and PR of the user while the user breathed into a plastic bag to create an environment where the user's O2 levels were depleted (i.e., to induce hypoxia), illustrating that the user was experiencing oxygen desaturation.

This disclosure, in various embodiments, configurations and aspects, includes components, methods, processes, systems, and/or apparatuses as depicted and described herein, including various embodiments, sub-combinations, and subsets thereof. This disclosure contemplates, in various embodiments, configurations and aspects, the actual or optional use or inclusion of, e.g., components or processes as may be well-known or understood in the art and consistent with this disclosure though not depicted and/or described herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that the appended claims should cover variations in the ranges except where this disclosure makes clear the use of a particular range in certain embodiments.

The terms "determine", "calculate" and "compute," and variations thereof, as used herein, are used interchangeably and include any type of methodology, process, mathematical operation or technique.

This disclosure is presented for purposes of illustration and description. This disclosure is not limited to the form or forms disclosed herein. In the Detailed Description of this disclosure, for example, various features of some exemplary embodiments are grouped together to representatively describe those and other contemplated embodiments, configurations, and aspects, to the extent that including in this disclosure a description of every potential embodiment, variant, and combination of features is not feasible. Thus, the features of the disclosed embodiments, configurations, and aspects may be combined in alternate embodiments, configurations, and aspects not expressly discussed above. For example, the features recited in the following claims lie in less than all features of a single disclosed embodiment, configuration, or aspect. Thus, the following claims are hereby incorporated into this Detailed Description, with each claim standing on its own as a separate embodiment of this disclosure.

Advances in science and technology may provide variations that are not necessarily express in the terminology of this disclosure although the claims would not necessarily exclude these variations.

What is claimed is:

1. An intraoral device, comprising:
a mouthpiece for receiving a dentition of a user, wherein the mouthpiece includes an infrared radiation emitter comprising ceramic nanoparticles embedded within the mouthpiece; and
an oxygen sensor for measuring an oxygen saturation level of the user's blood.

2. The intraoral device of claim 1, wherein the infrared radiation emitter is configured for dilating blood vessels of the user.

3. The intraoral device of claim 1, wherein the ceramic nanoparticles generate infrared radiation when exposed to heat from the user.

4. The intraoral device of claim 1, wherein the ceramic nanoparticles comprise boron silicate particles.

5. The intraoral device of claim 1, wherein the oxygen sensor comprises a pulse oximeter.

6. The intraoral device of claim 5, wherein the pulse oximeter is operative for measuring oxygen saturation levels of the user's blood.

7. The intraoral device of claim 5, wherein the pulse oximeter includes a photoplethysmography sensor for monitoring at least one of a cardiac condition, a respiratory condition, and a blood pressure condition of the user.

8. The intraoral device of claim 1, wherein the mouthpiece further includes a thermoelectric power source.

9. The intraoral device of claim 8, wherein the thermoelectric power source is operative for serving as a power source for at least one of the infrared radiation emitter and the oxygen sensor.

10. The intraoral device of claim 1, wherein the mouthpiece further includes electrodes operative for detecting electrical activity of the user's brain.

11. The intraoral device of claim 10, further comprising a microprocessor connected to the electrodes, wherein the microprocessor connected to the electrodes is operative as an electroencephalograph.

12. The intraoral device of claim 1, wherein the mouthpiece further includes a stimulator for sending an electrical impulse to a genioglossus muscle of the user.

13. The intraoral device of claim 12, wherein the electrical impulse is sent in response to an oxygen saturation level of the user's blood.

14. An intraoral device comprising:
a mouthpiece for being positioned in an oral cavity of a user, wherein the mouthpiece is customized to receive a dentition of the user and overlay the user's gingiva and buccal mucosa, and is operative for advancing a lower jaw of the user relative to an upper jaw of the user;
a photoplethysmography sensor secured to the mouthpiece, wherein the photoplethysmography sensor monitors at least one of a cardiac condition, a respiratory condition, perfusion index, heart rate variability, irregular heartbeat and a blood pressure condition of the user; and
comprising a plurality of ceramic nanoparticles embedded within the mouthpiece, the plurality of ceramic nanoparticles being configured to generate infrared radiation when exposed to the user's body heat.

15. The intraoral device of claim 14, wherein the infrared radiation dilates blood vessels of the user and the photoplethysmography sensor captures data indicative of regional oxygenation of the user's blood.

16. An intraoral device comprising:
a mouthpiece for being positioned in an oral cavity of a user;
a red light and infrared radiation emitter secured to the mouthpiece, wherein the red light and infrared radiation emitter comprises a plurality of ceramic nanoparticles embedded within the mouthpiece, and is configured for dilating blood vessels of the user;
a photoplethysmography sensor secured to the mouthpiece, wherein the photoplethysmography sensor configured to capture bio-signal measurements of the user indicative of a community disease; and
a thermoelectric power source configured to supply power to the red light and infrared radiation emitter and the photoplethysmography sensor.

17. The intraoral device of claim 16, wherein the thermoelectric power source captures a portion of the user's body heat and converts the captured portion of the user's body heat to direct current power.

* * * * *